United States Patent [19]
Hendren, III

[11] 3,983,996
[45] Oct. 5, 1976

[54] INSTRUMENT HOLDER

[76] Inventor: William Hardy Hendren, III, 76 Crafts Road, Brookline, Mass. 02146

[22] Filed: Oct. 6, 1975

[21] Appl. No.: 620,181

[52] U.S. Cl. .................................. 206/363; 21/90; 206/438; 206/477; 206/521
[51] Int. Cl.² ................. B65D 85/20; B65D 85/30; A61L 3/00
[58] Field of Search ............ 206/211, 317, 363–370, 206/377, 379, 438, 443, 477, 521, 523, 72; 211/60 R, 60 T; 21/83–90, 105, 82 R, 82 H,

[56] References Cited
UNITED STATES PATENTS

| | | | |
|---|---|---|---|
| 682,522 | 9/1901 | Boekel et al. ................... 21/105 X |
| 1,822,070 | 9/1931 | Vallone ......................... 211/60 T X |
| 2,462,475 | 2/1949 | DiFilippo ............................ 21/87 |
| 2,531,550 | 11/1950 | Bradley et al. ..................... 206/317 |
| 2,706,036 | 4/1955 | Neal .................................. 206/317 |
| 3,088,583 | 5/1963 | Holtz ............................ 206/523 X |
| 3,491,914 | 1/1970 | Elzey ............................ 206/365 X |
| 3,757,933 | 9/1973 | Banta ............................ 206/521 X |
| 3,807,954 | 4/1974 | McDonald ...................... 21/105 X |
| 3,836,043 | 9/1974 | Levin ............................ 206/521 X |

*Primary Examiner*—William Price
*Assistant Examiner*—Stephen Marcus
*Attorney, Agent, or Firm*—Thompson, Birch, Gauthier & Samuels

[57] ABSTRACT

A holder for a urological or other similar telescope having in its preferred embodiment a solid, plastic, rectangular body with cushioned ends, a lifting handle at one end, a lengthwise instrument recess shaped to hold the telescope, and retaining fingers pivotally mounted on the upper surface of the holder body, the retaining fingers pivoting to open and close the instrument recess.

In the alternate embodiment, instead of retaining fingers, a transversely sliding retainer block is used. The block has an angled slot which aligns with the top of the instrument recess in the open position and aligns with the bottom of the recess in the closed position.

10 Claims, 6 Drawing Figures

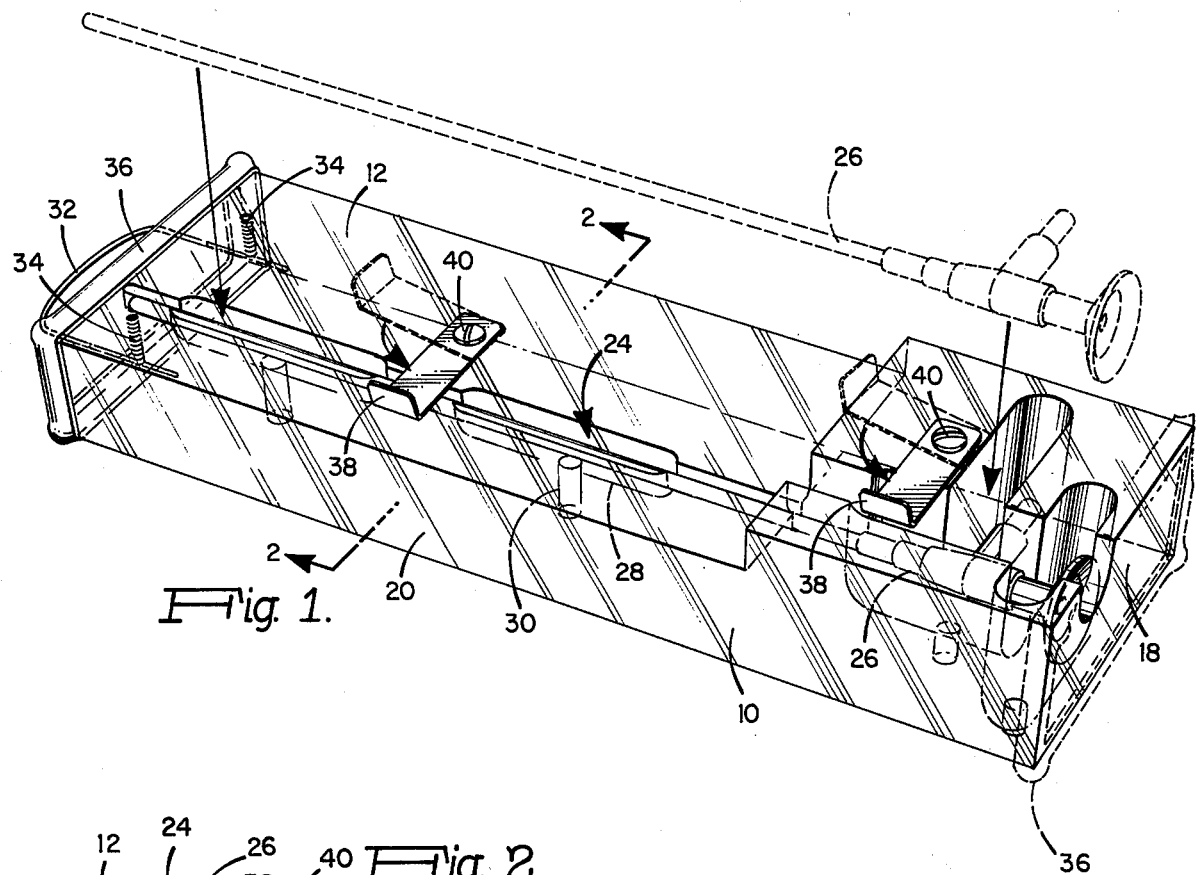
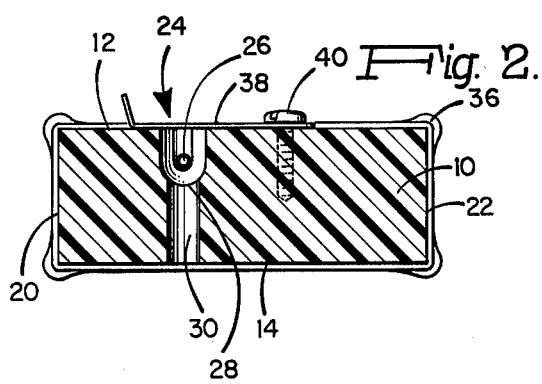
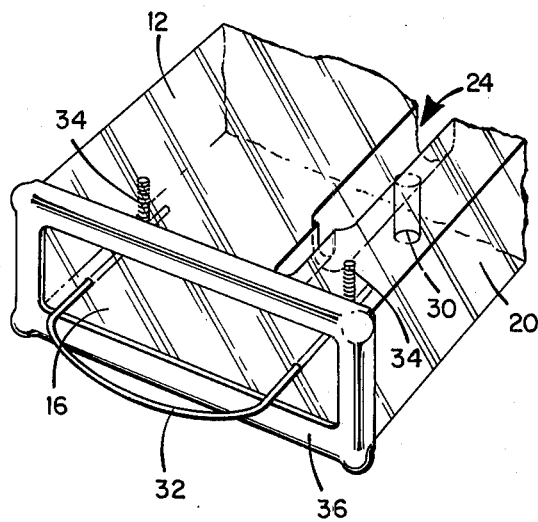

INSTRUMENT HOLDER

BACKGROUND OF THE INVENTION

In order to view the interior portions of hollow organs in the human body, surgeons and physicians use special telescopes which are extremely fragile and costly. These telescopes are particularly adapted for cystoscopy, bronchoscopy, esophagoscopy, peritoneoscopy, choledochoscopy and laryngoscopy. The telescopes usually have an eyepiece attached to a series of lighted lenses or quartz rods arranged to extend into the hollow organs to be viewed.

Typically, these telescopes are stored in open boxes which are lined with soft cotton or gauze material. Unfortunately, this arrangement has the disadvantage that the telescopes are subject to inadvertent bending and/or breaking when stored in this manner. Also, when the telescopes are used, especially during surgery, there is the added danger of breakage during the handling of the telescopes by various members of the surgical team. This handling occurs during sterilization, during periods of actual use on the patient, and during all of the other periods before, during and after surgical procedures.

The object of this invention is to provide an instrument holder in which the telescope can be sterilized and in which the telescope can be continuously stored except when the surgeon himself quickly and easily removes the telescope for use.

It is another object of this invention to provide an instrument holder which is relatively inexpensive to manufacture, is relatively unbreakable even if dropped, is capable of withstanding sterilization, is easy to open and close to remove and to secure the telescope, and which provides a safe and secure storage compartment for the telescope at all times.

SUMMARY OF THE INVENTION

This invention comprises an instrument holder which is specially designed to hold a urological telescope or the like. The holder is preferably made of unbreakable plastic which can withstand sterilization and which is in the shape of a rectangular solid. The holder has a recess which is shaped like the telescope it is designed to hold and has retaining fingers for securing the telescope in the recess or for permitting the telescope to be removed from the recess.

The holder has a lifting handle which can be grasped by a transfer forceps to facilitate sterilization and handling during surgery. The holder also has cushioned ends to reduce shock to the instrument in the event the holder is accidentally dropped.

DESCRIPTION OF THE DRAWINGS

FIG. 1 is a perspective view of the preferred embodiment of the holder showing the telescope secured in the instrument recess by the closed retaining fingers, and showing (in dotted) the telescope out of the instrument recess and opened retaining fingers.

FIG. 2 is a cross-section view taken along line 2—2 of FIG. 1, showing the telescope in the recess and closed retaining fingers.

FIG. 3 is a perspective view of the left end of the holder shown in FIG. 1. This view clearly illustrates the lifting handle and the cushioning pad.

DESCRIPTION OF THE PREFERRED AND ALTERNATE EMBODIMENTS

Figure 4:
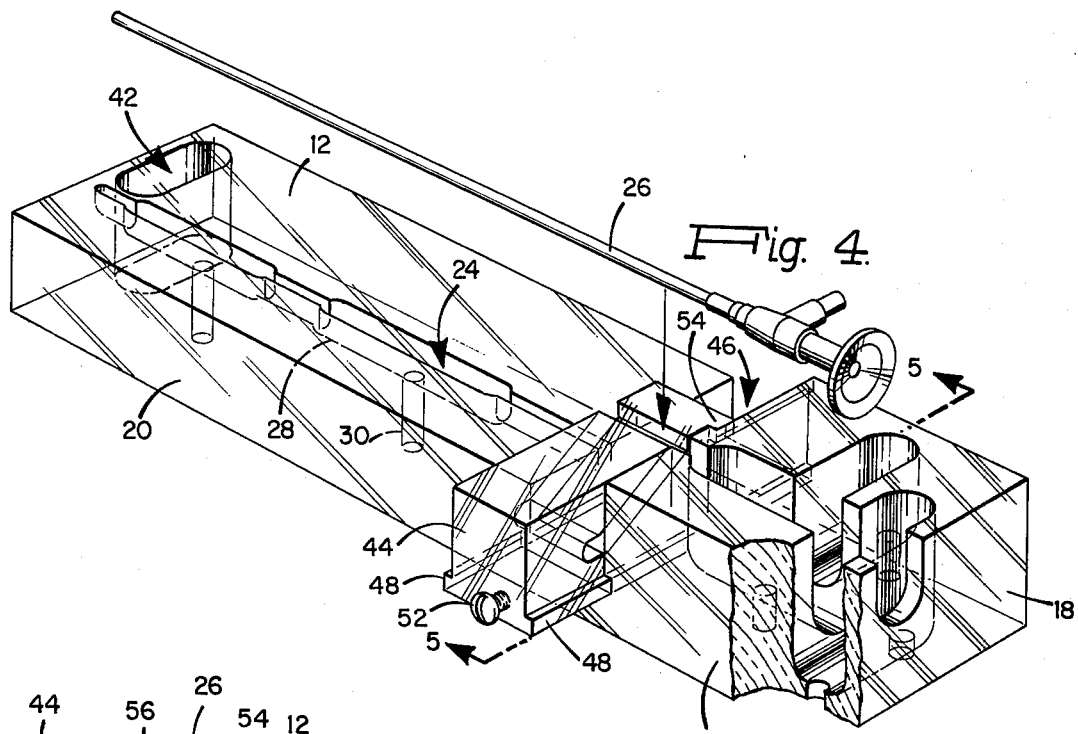
FIG. 4 is a perspective view of the alternate embodiment of the holder showing the telescope poised above the instrument recess and the retainer block in the open position, and showing (in dotted) the telescope secured in the recess and the retainer block in the closed position.
Figure 5:
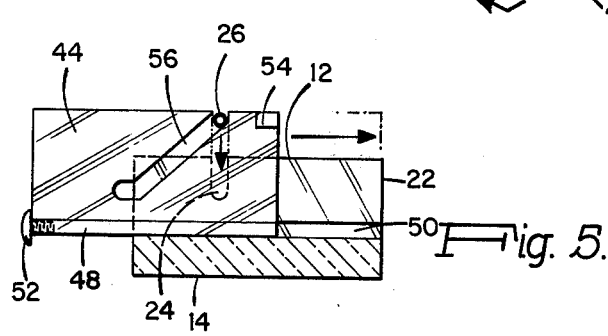
FIG. 5 is a cross-section view taken along line 5—5 of FIG. 4, showing the retainer block in the open position and the telescope disposed at the top of the instrument recess.
Figure 6:
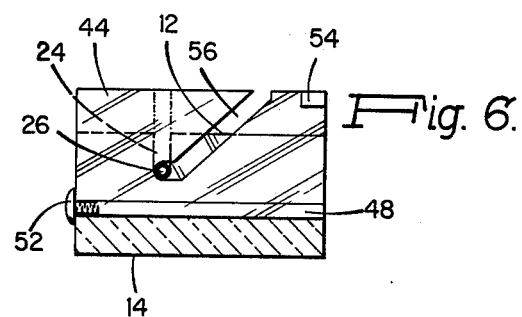
FIG. 6 is a cross-section view like FIG. 5 showing the retainer block in the closed position and the telescope secured in the bottom of the instrument recess.

The preferred embodiment of the instrument holder is shown in FIGS. 1-3. The alternate embodiment is shown in FIGS. 4-6. The only difference between these two embodiments is the nature of the retaining means and the nature of the lifting handle.

FIG. 1 shows the holder for a urological or other similar telescope which comprises a holder body 10 made from a solid block of synthetic plastic which is substantially unbreakable, substantially non-resilient, and heat-dissipating. The holder body has the approximate shape of a rectangular solid.

Holder body 10 is preferably at least three times as long as it is wide or deep. Holder body 10 has a stepped upper surface 12, a lower surface 14, a left end surface 16, a right end surface 18, a front side surface 20 and a rear side surface 22. The five surfaces 14, 16, 18, 20 and 22 are flat and unbroken in the preferred embodiment, except that upper surface 12 is stepped (optionally).

Upper surface 12 is machined or molded or otherwise formed so as to have an instrument recess 24 which has the outline, when viewed from above, of the telescope 26. Instrument recess 24 is oriented lengthwise and is at least half as long as the length of holder body 10. Also, recess 24 is formed with a plurality of spaced-apart depressions 28 into which the sterilizing fluid can drain and accumulate, as well as a plurality of drain holes 30 through which the accumulated fluid can drain out to the lower surface 14.

The holder body has a lifting handle 32 which, in the preferred embodiment, is made of a curved length of wire which is pinned into left end surface 16 of the holder body by threaded pins 34. The handle 32 is particularly useful during sterilization and during handling by transfer forceps.

The holder body is also fitted with resilient cushioning pads 36 at each end. These pads 36 are preferably removable for purposes of sterilization and could be of a disposable nature. Their purpose is to reduce the shock transmitted to the stored telescope in the event that the holder is accidentally dropped.

The retaining means of the preferred embodiment shown in FIGS. 1-3 will now be described. Two retaining fingers 38 having upturned ends are pivotally attached by threaded bolts 40 to the upper surface 12. The fingers 38 can be manually pivoted between an open position shown in dotted in FIG. 1, and a closed position shown in full in FIG. 1. In the open position, the instrument recess 24 is not obstructed by fingers 38 and the telescope 26 can be inserted into or withdrawn from the recess. In the closed position, the recess 24 is bridged or blocked by the fingers 38 and the telescope is secured in the holder. The fingers 38 are easily shifted by manually engaging the upturned end portions of the fingers.

The alternate embodiment of this invention is shown in FIGS. 4-6. It will be seen that wire lifting handle 32 has been replaced by a flattened aperture 42 which extends through the holder body adjacent to the left end surface 16. The axis of the aperture 42 is perpendicular to upper surface 12 of the holder body.

It will also be seen that retaining fingers 38 have been replaced by a retainer block 44 which slides in a transverse opening 46. The transverse opening 46 extends between front side surface 20 and rear side surface 22 and opens at these two surfaces plus upper surface 12. The retainer block has protruding lower flanges 48 which dovetail with and slide in similarly shaped recesses 50 formed in the transverse opening 46. A bolt 52 is mounted in retainer block 44 and limits the retainer block travel towards rear side surface 22. A lip 54 protrudes from retainer block 44 and engages a similarly shaped lip in the transverse opening 46 to limit the retainer block travel towards front side surface 20.

FIG. 5 shows the retainer block 44 in the open position. The block has an angled slot 56 which is parallel to the side surfaces, when viewed from above, and which is angled down and to the left, when viewed from the end (as in FIG. 5). Telescope 26 is shown at the top of slot 56 and at the top of instrument recess 24, which tops are both aligned in the open position shown in FIG. 5. As the retainer block 44 is manually pushed towards the closed position shown in FIG. 6, the telescope 26 is lowered gently to the bottoms of the instrument recess 24 and the slot 56, which bottoms are both aligned in the closed position shown in FIG. 6.

It will be seen in FIG. 6 that the telescope 26 is prevented from falling out of the holder in the closed position by the alignment arrangement of the retainer block slot and the instrument recess.

The holder is designed to be used as a shipping container by the telescope manufacturer. Thereafter, the telescope is normally kept at all times in the holder until it is needed by the physician or surgeon. The telescope is sterilized in the holder by various means, such as in a germicidal liquid solution, in steam or in ethylene oxide gas. The holder is then removed from the sterilizing vessel and transported by the use of transfer forceps in engagement with the lifting handle. During surgery or other procedure requiring use of the telescope, the surgeon or physician (or assistant) manually opens the retaining fingers (or pushes the retainer block to the open position), and picks out the telescope or inverts the holder to drop the telescope out of the holder. When the telescope is no longer needed, it is replaced into the instrument recess and the retaining fingers are manually closed (or the retainer block is pushed to the closed position).

It will be appreciated that the holder keeps the telescope secure from breakage at all times when it is not actually being used which is very important in view of the delicate nature and cost of such telescopes. The holder also provides a positive positioning means for the telescope whereby the user knows the exact position of the telescope when he wants to grasp it.

The above description obviously suggests many possible variations and modifications of this invention which would not depart from its spirit and scope. It should be understood, therefore, that the invention is not limited in its application to the details of structure specifically described or illustrated and that within the scope of the appended claims, it may be practiced otherwise than as specifically described or illustrated.

I claim:

1. A sterilizable holder for a urological or other telescope comprising:
   a. a coverless, elongated holder body made of a solid, substantially unbreakable, substantially non-resilient, sterilizable, heat-dissipating, synthetic plastic material;
   b. said holder body having a lifting handle associated therewith to facilitate handling and sterilizing;
   c. said holder body having a substantially flat, uncovered upper surface which is at least three times as long as it is wide;
   d. said holder body having a lengthwise instrument holding recess formed in said upper surface, said instrument recess being at least one half as long as said holder body upper surface, said instrument recess having a profile, when viewed from above, of the urological or other telescope which it is adapted to hold;
   e. said instrument holding recess having fluid drainage means formed therein for permitting sterilizing fluid to drain from said recess; and
   f. retaining means associated with said holder body, said retaining means having an open position in which said instrument recess is entirely unobstructed to permit the telescope to be freely placed in or removed from said instrument recess, said retaining means having a closed position in which said instrument recess is partially obstructed to secure the telescope in said instrument recess while permitting the sterilizing fluid to freely circulate, said retaining means being manually operated.

2. The holder of claim 1 wherein said telescope holder functions as a manufacturer's shipping container, and as a nurse's sterilizing container, and as a surgeon's operating room protective container.

3. The holder of claim 1 wherein said fluid drainage means includes a plurality of drain holes formed in said holder body, said drain holes communicating between the bottom of said instrument recess and the lower surface of said holder body.

4. The holder of claim 1 wherein said lifting handle comprises a separate elongated member which is affixed to and extends from one end of said holder body.

5. The holder of claim 1 further having resilient cushioning pads removably affixed to at least some of the exterior surfaces of said holder body.

6. The holder of claim 1 wherein said retaining means comprises at least one finger which is movably mounted on said upper surface of said holder body, said finger moving between an open position wherein said instrument recess is clear, and a closed position wherein said instrument recess is blocked.

7. The holder of claim 6 wherein said finger is pivotally mounted.

8. The holder of claim 1 wherein said holder body has an exterior shape which approximates a rectangular solid.

9. The holder of claim 1 wherein said lifting handle comprises a slot which is formed through said holder body adjacent to one end thereof.

10. The holder of claim 1 wherein said retaining means comprises a transverse opening formed in said upper surface of said holder body, said transverse opening extending between and opening at two side surfaces of said holder body, and a retainer block slidably engaged within said transverse opening and being transversely moved between an open and a closed position, said retainer block having a slot which aligns with the top of said instrument recess only when said retainer block is in the open position, said slot being angled downwardly so that it aligns with the bottom of said instrument recess only when said retainer block is in the closed position.

* * * * *